(12) United States Patent
Kleiner et al.

(10) Patent No.: US 8,961,589 B2
(45) Date of Patent: Feb. 24, 2015

(54) BIOABSORBABLE COATING WITH TUNABLE HYDROPHOBICITY

(75) Inventors: Lothar W. Kleiner, Los Altos, CA (US); John Stankus, Campbell, CA (US); Nam D. Pham, San Jose, CA (US); Michael H. Ngo, San Jose, CA (US); Bozena Zofia Maslanka, Aptos, CA (US); Syed Faiyaz Ahmed Hossainy, Fremont, CA (US); Mikael Trollsas, San Jose, CA (US); Yiwen Tang, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1323 days.

(21) Appl. No.: 11/888,807

(22) Filed: Aug. 1, 2007

(65) Prior Publication Data
US 2009/0036978 A1    Feb. 5, 2009

(51) Int. Cl.
  *A61F 2/82*    (2013.01)
  *A61L 31/16*    (2006.01)
  *A61L 31/10*    (2006.01)
  *A61L 31/14*    (2006.01)

(52) U.S. Cl.
  CPC .................. *A61L 31/16* (2013.01); *A61L 31/10* (2013.01); *A61L 31/148* (2013.01); *A61L 2300/416* (2013.01)
  USPC .......................... 623/1.42; 623/1.44; 623/1.46

(58) Field of Classification Search
  None
  See application file for complete search history.

(56) References Cited

U.S. PATENT DOCUMENTS

| 5,962,007 | A  | * | 10/1999 | Cooper et al. ................ 424/426 |
| 7,223,553 | B2 |   | 5/2007  | Roberts et al. |
| 2002/0173595 | A1 | * | 11/2002 | Pohjonen et al. ............. 525/411 |
| 2003/0065382 | A1 | * | 4/2003  | Fischell et al. ............... 623/1.15 |
| 2003/0144727 | A1 | * | 7/2003  | Rosenthal et al. ........... 623/1.15 |
| 2004/0073297 | A1 | * | 4/2004  | Rohde et al. ................. 623/1.46 |
| 2005/0129731 | A1 |   | 6/2005  | Horres et al. |
| 2006/0034888 | A1 |   | 2/2006  | Pacetti et al. |
| 2006/0141548 | A1 |   | 6/2006  | Roberts et al. |
| 2006/0194829 | A1 |   | 8/2006  | Clackson et al. |
| 2006/0229711 | A1 | * | 10/2006 | Yan et al. ..................... 623/1.38 |
| 2007/0212386 | A1 | * | 9/2007  | Patravale et al. ............. 424/422 |
| 2007/0218102 | A1 |   | 9/2007  | Chudzik et al. |

FOREIGN PATENT DOCUMENTS

| EP | 1 832 289       | 9/2007 |
| WO | WO 2005/051445  | 6/2005 |
| WO | WO 2006/014270  | 2/2006 |
| WO | WO 2006/023672  | 3/2006 |

OTHER PUBLICATIONS

Jundt et al. "A rapamycin derivative (everolimus) controls proliferation through down-regulation of truncated CCAAT enhancer binding protein β and NF-kB activity in Hodgkin and anaplastic large cell lymphomas", Blood vol. 106, No. 5, pp. 1801-1807 (2005).

Vitko et al., "Everolimus with Optimized Cyclosporine Dosing in Renal Transplant Recipients: 6-Month Safety and Efficacy Results of Two Randomized Studies", Am. J. of Transplantation 4, pp. 626-635 (2004).

International Search Report for PCT/US2008/071380, mailed Oct. 28, 2009, 14 pgs.

Multanen et al., "Bacterial adherence to afloxacin-blended polylactone-coated self-reinforced L-lactic acid polymer urological stents", BJU International 86, pp. 966-969 (2000).

* cited by examiner

*Primary Examiner* — Anna Pagonakis
*Assistant Examiner* — Rebecca Preston
(74) *Attorney, Agent, or Firm* — Squire Patton Boggs (US) LLP

(57) ABSTRACT

The present invention relates to implantable medical devices coated with polymer having tunable hydrophobicity and their use in the treatment of vascular diseases.

7 Claims, No Drawings

BIOABSORBABLE COATING WITH TUNABLE HYDROPHOBICITY

FIELD OF THE INVENTION

This invention relates to the fields of organic chemistry, polymer science, material science and medical devices. In particular, it relates to a medical device having a bioabsorbable coating with tunable hydrophobicity for treating vascular diseases.

BACKGROUND OF THE INVENTION

Percutaneous transluminal coronary angioplasty (PTCA) is a common procedure for treating heart disease. A problem associated with the PTCA includes the formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Biological therapy can be achieved by medicating the stents. Medicated stents provide for the local administration of a therapeutic substance at the desired site. Local delivery produces fewer side effects and achieves more favorable results.

However, the use of drug eluting stents (DESs) has resulted in a new problem, late stent thrombosis, the forming of blood clots long after the stent is in place. It was deduced that the formation of blood clots was most likely due to delayed healing which was postulated to be a side-effect of the use of cytostatic drugs.

Another potential shortcoming of the foregoing method of medicating stents is the control of the release rate of a therapeutic agent. The active agent can be released from a stent by either diffusion, or swelling followed by diffusion and degradation or erosion. The hydrophobicity of the polymer is critical in dissolving the therapeutic agent. The commonly used therapeutic agents have limited or low solubility posing a serious obstacle for the drug's release kinetics from a stent. Thus, there is a need to maximize the solubility of a therapeutic agent in the polymer and to optimize the release rate of a therapeutic agent.

To address the above situation, stents can be fabricated from materials that are biocompatible, biodegradable and, if desired, bio-absorbable. The goal is for the stent to have a biocompatible coating which demonstrates great safety with regard to stent thrombosis. Ideally, the stent coatings should preferably lower acute and sub-acute thrombosis rates. The coating material selected must not only have sufficient mechanical properties but also show excellent coating integrity. The preceding problem has been at least partially ameliorated by the use of increasingly biocompatible materials and/or biocompatible coating.

What is needed is an implantable medical device that includes a polymer coating which maximizes the solubility of a therapeutic agent in the polymer and optimizes the release rate of a therapeutic agent. While this would be particularly useful with regard to coronary stents, it would also provide substantial benefit to any manner of implantable medical devices. Such implantable medical devices for use as drug delivery systems should also demonstrate excellent mechanical properties when implanted in a patient. The present invention provides such implantable medical devices.

SUMMARY OF THE INVENTION

Thus, in one aspect, the current invention relates to an implantable medical device, comprising:
a device body;
an optional primer layer disposed over the device body;
a drug reservoir layer disposed over the device body or the primer layer, if opted,
wherein the drug reservoir layer comprises a polymer and one or more therapeutic agent(s) and further wherein the hydrophobicity of the polymer is matched to that of the therapeutic agent(s).

In an aspect of this invention, the polymer is a copolymer comprising a first monomer selected from the group consisting of L-lactide, D-lactide, D,L-lactide and meso-lactide and a second monomer selected from the group consisting of lactone, ε-caprolactone, δ-valerolactone, 1,4-dioxan-2-one, 1,5-dioxepan-2-one, 1,4,6-trioxaspiro[4.4]nonane and trimethyl carbonate, wherein
the first monomer, the second monomer or both is/are optionally substituted with a moiety selected form the group consisting of $C_1$-$C_{20}$ alkyl, $C_2$-$C_{20}$ alkenyl, $C_3$-$C_8$ cycloalkyl, $C_6$-$C_{10}$ aryl, partially or fully fluorinated derivatives of any of the preceding and combinations thereof so as to match the hydrophobicity of the polymer to that of the therapeutic agent.

In an aspect of this invention, the therapeutic agent is everolimus.

In an aspect of this invention, the polymer is selected from the group consisting of poly(L-lactide-co-ε-caprolactone) and poly(L-lactide-co-trimethylene carbonate).

In an aspect of this invention, the polymer comprises poly(L-lactide-co-ε-caprolactone) polymer.

In an aspect of this invention, the poly(L-lactide-co-ε-caprolactone) constitutional unit molar ratio is from about 70:30 to about 50:50.

In an aspect of this invention, the poly(L-lactide-co-ε-caprolactone) has a average molecular weight from about 50,000 to about 500,000 Daltons.

In an aspect of this invention, the poly(L-lactide-co-ε-caprolactone) has a solubility parameter less than about 11.5 $(cal/cm^3)^{1/2}$.

In an aspect of this invention, the drug reservoir layer has a coating thickness from about 1 um to about 10 um.

In an aspect of this invention, the drug to polymer wt/wt ratio is from about 1.0:0.5 to about 1.0:10.0.

In an aspect of this invention, the drug dose is from about 5-200 microgram/$cm^2$ to about 20-100 microgram/$cm^2$.

In an aspect of this invention, the implantable medical device is a stent,

An aspect of this invention is a method of treating a vascular disease, comprising:
deploying in the vasculature of a patient in need thereof an implantable medical device, wherein the device comprises:
a device body;
an optional primer layer disposed over the device body;
a drug reservoir layer disposed over the device body or the primer layer, if opted, wherein the drug reservoir layer comprises a polymer and one or more therapeutic agent(s) and further wherein the hydrophobicity of the polymer is matched to that of the therapeutic agent(s).

In an aspect of this invention, the polymer is a copolymer comprising a first monomer selected from the group consisting of L-lactide, D-lactide, D,L-lactide and meso-lactide and a second monomer selected from the group consisting of lactone, ε-caprolactone, δ-valerolactone, 1,4-dioxan-2-one, 1,5-dioxepan-2-one, 1,4,6-trioxaspiro[4.4]nonane and trimethyl carbonate, wherein the first monomer, the second monomer or both is/are optionally substituted with a moiety selected form the group consisting of $C_1$-$C_{20}$ alkyl, $C_2$-$C_{20}$ alkenyl, $C_3$-$C_8$ cycloalkyl, $C_6$-$C_{10}$ aryl, partially or fully fluorinated derivatives of any of the preceding and combinations thereof so as to match the hydrophobicity of the polymer to that of the therapeutic agent.

In an aspect of this invention, the therapeutic agent is everolimus.

In an aspect of this invention, the polymer is selected from the group consisting of poly(L-lactide-co-ε-caprolactone) and poly(L-lactide-co-trimethylene carbonate).

In an aspect of this invention, the polymer comprises poly (L-lactide-co-ε-caprolactone) polymer.

In an aspect of this invention, the poly(L-lactide-co-ε-caprolactone) constitutional unit molar ratio is from about 70:30 to about 50:50.

In an aspect of this invention, the poly(L-lactide-co-ε-caprolactone) has a average molecular weight from about 50,000 to about 500,000 Daltons.

In an aspect of this invention, the poly(L-lactide-co-ε-caprolactone) has a solubility parameter less than about 11.5 $(cal/cm^3)^{1/2}$.

In an aspect of this invention, the drug reservoir layer has a coating thickness from about 1 um to about 10 um.

In an aspect of this invention, the drug to polymer wt/wt ratio is from about 1.0:0.5 to about 1.0:10.0.

In an aspect of this invention, the drug dose is from about 5-200 microgram/$cm^2$ to about 20-100 microgram/$cm^2$.

In an aspect of this invention, the implantable medical device is a stent,

In an aspect of this invention, the vascular disease is atherosclerosis.

In an aspect of this invention, the vascular disease is restenosis.

In an aspect of this invention, the vascular disease is vulnerable plaque.

In an aspect of this invention, the vascular disease is peripheral vascular disease.

In an aspect of this invention, the vascular disease is late stent thrombosis.

DETAILED DESCRIPTION OF THE INVENTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts.

An implantable medical device specifically designed and intended solely for the localized delivery of a therapeutic agent is within the scope of this invention.

As used herein, "device body" refers to a fully formed implantable medical with an outer surface to which no coating or layer of material different from that of which the device itself is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Implantable medical devices may also be made of polymers that are biocompatible and biostable or biodegradable, the latter term including bioabsorbable and/or bioerodable.

As used herein, "biocompatible" refers to a polymer that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

Among useful biocompatible, relatively biostable polymers are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an arterial wall thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, "optional" means that the element modified by the term may or may not be present. For example, without limitation, a device body (db) that has coated on it an "optional" primer layer (pl), and a drug reservoir layer (dr) refers, without limitation, to any of the following devices: db+pl+dr and db+dr.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include acrylate and methacrylate polymers with poly(n-butyl methacrylate) being a presently preferred primer. Some additional examples of primers include, but are not limited to, poly (ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

As use herein, a material that is described as a layer "disposed over" an indicated substrate, e.g., without limitation, a device body or another layer, refers to a relatively thin coating of the material applied, preferably at present, directly to essentially the entire exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. For the purpose of this invention, the drug reservoir layer also acts as rate-controlling layer. As used herein, "rate-controlling layer" refers to a polymer layer that controls the release of therapeutic agents or drugs into the environment. While any polymer may be used to construct a drug reservoir layer of this invention, particularly useful polymers include, but not limited to, poly(L-lactide-co-ϵ-caprolactone) and poly(L-lactide-co-trimethylene carbonate).

As used herein, "hydrophobic" refers to a polymer that lacks an affinity for water. That is, it tends to repel water, to not dissolve in, mix with or be wetted by water or to do so only to a very limited degree and to not absorb water or, again, to do so only to a very limited degree. With regard to polymers, generally hydrophobicity increase with increasing alkyl content in the polymer backbone, that is, the greater the alkyl content in one or more of the constitutional units of the polymer. The hydrophobicity of a polymer may be characterized by determining the static contact angle of droplets of distilled water on a surface of the polymer. The greater the contact angle, the more hydrophobic the polymer. Generally speaking, a contact angle of greater than 90° indicates a hydrophobic polymer. The specifics or such measurements will not be presented here since they are well-known to those skilled in the art.

As used herein, "contact angle" is defined as an angle at the tangent of a droplet in a fluid phase that has taken an equilibrium shape on a solid surface under ambient condition.

The biodegradable hydrophobic polymers herein contain water-labile bonds interconnecting the constitutional units of the polymer. The water-labile bonds include, without limitation, esters, orthoesters, anhydrides and imides. Other bonds such as, without limitation, ethers, amides, urethanes, etc. may also be present in the polymer but the propensity of the polymer to surface erosion rather than bulk erosion relates to the overall hydrophobicity of the polymer and the content and reactivity of the water-labile linkages in the polymer. That is, the overall hydrophobic nature of the polymer precludes or at least inhibits the incursion of water into the polymer's interior while water-labile linkages exposed on the polymer's surface hydrolyze resulting in the degradation of the polymer from the outermost surface of the bulk polymer, be it a device made of the polymer or a coating of the polymer on a device, inward rather than by bulk mode erosion.

Suitable hydrophobic polymers include, without limitation, poly(vinyl acetate), poly(ethylene-co-vinyl acetate), poly(vinyl acetals) such as poly(vinyl butyral) (e.g., BUT- VAR), poly(meth)acrylates, for example, poly(methyl methacrylate), poly(ethyl methacrylate), poly(n-propyl methacrylate), poly(iso-propyl methacrylate), poly(n-butyl methacrylate), copolymers of butyl n-methacrylate with non-polar monomers (e.g., poly(ethyl methacrylate-co-n-butyl methacrylate)), poly(iso-butyl methacrylate), poly(methyl acrylate), poly(ethyl acrylate), poly(n-propyl acrylate), poly (iso-propyl acrylate), poly(n-butyl acrylate), poly(iso-butyl acrylate), styrene-butadiene-styrene triblock copolymers, styrene-ethylene/butylene-styrene triblock copolymers (e.g., KRATON available from Shell Oil Co. of Houston, Tex.), styrene-isobutylene-styrene triblock copolymers, parylene-C, organosilicon polymers (e.g., ELASTEON), and halogenated (e.g., fluorinated or chlorinated) polymers such as poly (vinyl chloride), poly(vinyl fluoride), poly(vinylidene chloride), poly(vinylidene fluoride) (e.g., KYNAR available from Atofina Chemicals, Inc. of Philadelphia, Pa.), poly (hexafluoropropene), poly(vinylidene fluoride-co-hexafluoropropene) (e.g., SOLEF available from Solvay S.A. of Brussels, Belgium), poly(ethylene-co-hexafluoropropene), and various grades of amorphous TEFLON, including polytetrafluoroethylene (available from E.I. Du Pont de Nemours & Co. of Wilmington, Del.), BUTVAR is a trade name of poly (vinyl butyral) (available from Solutia, Inc. of St. Louis, Mo.), ELASTEON is the trade name of the block copolymer of methylene diphenyl diisocyanate, 1,4-butanediol, polyhexamethyleneglycol, and a carbinol terminated polydimethylsiloxane (manufactured by AorTech Biomaterials Co. of Chatswood, Australia), poly[trimellitylimido-L-tyrosine-co-sebacic acid-co-1,3-bis(para-carboxyphenoxy)propane] p(TMIT-SBA-PCPP), poly[1,6-bis(para-carboxyphenoxy)-hexane-co-di-ortho-carboxyphenoxy sebacateanhydride] p(PCPX-OCPSA), poly[1,3-bis(para-carboxyphenoxy) propane-co-salicylic acid-co-sebacic acid] p(PCPP-SBA-SA), poly(maleic acid-co-sebacic acid), p(MA-SBA), poly(L-lactic acid-co-L-aspartic acid), p(LLA-LAspA), poly(DL-lactic acid-co-L-aspartic acid) p(DLLA-LAspA), poly(L-lactic acid) pLLA, poly(DL-lactic acid) pDLLA, poly(L-lactic acid-co-ethylene glycol) p(LLA-EG), poly(DL-lactic acid-co-ethylene glycol) p(DLLA-EG), poly(ethylene glycol-co-butylene terephthalate) p(EG-BT), poly(4-hydroxy-L-proline ester) p(HOXPE), poly(1,10-decanediol-co-L-latic acid) p(DCD-LLA), poly(1,10-decanodiol-co-D,L-lactic acid) p(DCD-DLLA), poly(1,2,6-hexanetriol-co-trimethylorthoacetate) p(HTOL-TMAC), poly(hydroxybutyrate) (PHB), poly(hydroxyvalerate) (PHV), poly(hydroxy-butyrate-valerate) (PHBV), poly(L-lactide-co-ε-caprolactone) and poly(L-lactide-co-trimethylene carbonate).

As used herein, "alkyl" refers to a straight or branched chain fully saturated (no double or triple bonds) hydrocarbon (carbon and hydrogen only) group. The alkyl groups of this invention may range from $C_1$ to $C_{20}$, preferably $C_2$ to $C_{10}$ and currently most preferably $C_3$ to $C_8$. Examples of alkyl groups include, but are not limited to, methyl, ethyl, propyl, isopropyl, butyl, isobutyl, tertiary butyl, pentyl, hexyl, heptyl, octyl, nonyl and decyl.

As used herein, "alkenyl" refers to an alkyl group that contains in the straight or branched hydrocarbon chain one or more double bonds. The alkyl groups of this invention may range from $C_2$ to $C_{20}$, preferably $C_2$ to $C_{10}$ and currently most preferably $C_3$ to $C_8$. Examples of alkenyl groups include, but are not limited to, ethenyl, propenyl, isopropenyl, butenyl, isobutenyl, tertiary butenyl, pentenyl, hexenyl, heptenyl, octenyl, nonenyl and decenyl.

As use herein, "cycloalkyl" group refers to an alkyl group in which the end carbon atoms of the alkyl chain are covalently bonded to one another in the ring so formed. The cycloalkyl groups of this invention may range from $C_3$ to $C_8$, preferably $C_3$ to $C_6$ and currently most preferably $C_3$ to $C_5$. Examples of alkyl groups include, but are not limited to, for instance, $C_3$-$C_8$ cycloalkyl group refers to a three, four, five, six, seven or eight member ring, that is, cyclopropane, cyclobutane, cyclopentane, cyclohexane, cycloheptane and cyclooctane.

As used herein, "aryl" refers to a carbocyclic (all carbon) ring or two or more fused rings (rings that share two adjacent carbon atoms) that have a fully delocalized pi-electron system and from 6 to 14 carbon atoms in the ring(s). The aryl groups of this invention may range from $C_6$ to $C_{14}$, preferably $C_6$ to $C_{12}$ and currently most preferably $C_6$ to $C_{10}$. Examples of aryl groups include, but are not limited to, benzene, naphthalene, anthracene and azulene.

As used herein, the following graphic representation of a polymer:

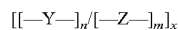

refers to a regular alternating, a random or a block, preferably at present random, copolymer. As use herein, the letters "n" and "m" connote mole fractions of the constitutional units Y and Z and n+m=1. The letter "x" connotes sequence multiplicity, that is, the number of repeats of the entity within the outside brackets in the polymer.

While any polymer capable of being chemically manipulated as set forth herein to match its hydrophobicity to that of selected therapeutic agent may be used to construct a drug reservoir layer of this invention. The presently preferable polymer used in this invention is a copolymer comprising at least two monomers. Examples of first monomer useful for the purposes of this invention include, without limitation, L-lactide, D-lactide, D,L-lactide and meso-lactide. The first monomer is optionally substituted with a moiety selected form the group consisting of $C_1$-$C_{20}$ alkyl, $C_2$-$C_{20}$ alkenyl, $C_3$-$C_8$ cycloalkyl, $C_6$-$C_{10}$ aryl, partially or fully fluorinated derivatives of any of the preceding and combinations thereof so as to match the hydrophobicity of the polymer to that of the therapeutic agent.

The second monomer selected from the group consisting of lactone, ε-caprolactone, δ-valerolactone, 1,4-dioxan-2-one, 1,5-dioxepan-2-one, 1,4,6-trioxaspiro[4.4]nonane and trimethyl carbonate. The second monomer is optionally substituted with a moiety selected form the group consisting of $C_1$-$C_{20}$ alkyl, $C_2$-$C_{20}$ alkenyl, $C_3$-$C_8$ cycloalkyl, $C_6$-$C_{10}$ aryl, partially or fully fluorinated derivatives of any of the preceding and combinations thereof so as to match the hydrophobicity of the polymer to that of the therapeutic agent. Examples of second monomer useful for the purposes of this invention include, without limitation:

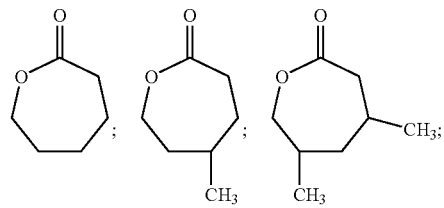

-continued

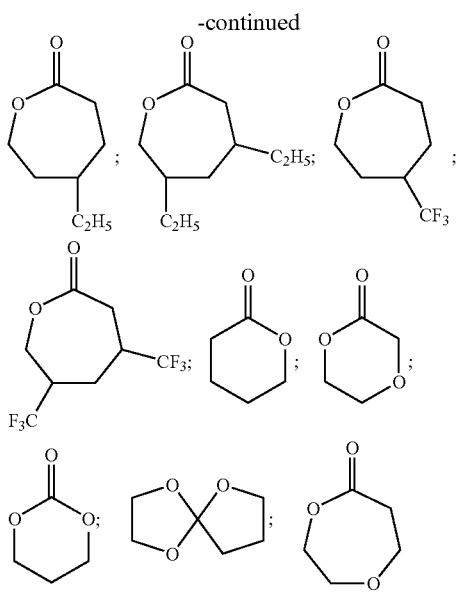

Suitable polymers of the present invention include, but not limited to, poly(L-lactide-co-ε-caprolactone) and poly(L-lactide-co-trimethylene carbonate).

As used herein, "constitutional unit" refers to monomer component unit of the polymer moiety. The poly(L-lactide-co-ε-caprolactone) constitutional unit molar ratio for a presently preferred polymer of this invention is from about 70:30 to about 50:50.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "treating" refers to the administration of a therapeutically effective amount of a therapeutic agent to a patient known or suspected to be suffering from a vascular disease. A "therapeutically effective amount" refers to that amount of a therapeutic agent that will have a beneficial affect, which may be curative or palliative, on the health and well-being of the patient with regard to the vascular disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery, or loss of organ function if the artery is peripheral.

"Restenosis" refers to the re-narrowing or blockage of an artery at or near the site where angioplasty or another surgical procedure was previously performed to remove a stenosis. It is generally due to smooth muscle cell proliferation and, at times, is accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to smooth muscle cell proliferation. There were also issues of acute reclosure due to vasospasm, dissection, and thrombosis at the site of the procedure. Stents eliminated acute closure from vasospasm and greatly reduced complications from dissections. While the use of IIb-IIIa anti-platelet drugs such as abciximab and epifabatide, which are anti-thrombotic, reduced the occurrence of post-procedure clotting (although stent placement itself can initiate thrombosis). Stent placement sites are also susceptible to restenosis due to abnormal tissue growth at the site of implantation. This form of restenosis tends also to occur at 3 to 6 months after stent placement but it is not affected by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time. To date these stents comprised delivery interfaces (lengths) that are less than 40 mm in length and, in any event, have delivery interfaces that are not intended, and most often do not, contact the luminal surface of the vessel at the non-afflicted region at the periphery of the afflicted region.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage-derived enzyme degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

"Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to brain, it causes a stroke.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

Suitable therapeutic agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2-hydroxyethyl)rapamycin (EVEROLIMUS®), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, haloprednone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Suitable antiallergic agents include, without limitation, permirolast potassium. Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethyl-rapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred therapeutic agents include corticosteroids, everolimus, zotarolimus, sirolimus, sirolimus derivatives, paclitaxel, bisphosphonates, ApoA1, mutated ApoA1, ApoA1 milano, ApoA1 mimetic peptides, ABC A1 agonists, anti-inflammatory agents, anti-proliferative agents, anti-angiogenic agents, matrix metalloproteinase inhibitors and tissue inhibitors of metalloproteinases.

As used herein, "hydrophobicity" can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

Accordingly, for the practice of the present invention, whether a material is hydrophobic or hydrophilic is relative. Between different materials, whichever has a lower Hildebrand value (δ) value compared to the δ value of the other is designated as a hydrophobic, and the material with higher Hildebrand value (δ) value is designated as a hydrophilic. In one embodiment, the δ value defining the boundary between hydrophobic and hydrophilic can be about 11.5 $(cal/cm^3)^{1/2}$. According to this embodiment, hydrophobic is defined as having a δ value equal to or below about 11.5 $(cal/cm^3)^{1/2}$, and hydrophilic is defined as having a δ value of about 11.5 $(cal/cm^3)^{1/2}$ or higher. Measurements other than Hildebrand value can also be used to determine the hydrophobicity of the material.

With regard to the present invention, poly(L-lactide-co-ϵ-caprolactone) and poly(L-lactide-co-trimethylene carbonate), are presently preferred hydrophobic polymers of the drug reservoir layer.

With regard to the present invention, everolimus, an immunosuppressive macrolide antibiotic, is a presently preferred therapeutic agent.

The hydrophobicity of polymers, poly(L-lactide-co-ϵ-caprolactone) and poly(L-lactide-co-trimethylene carbonate) and a therapeutic agent, everolimus was calculated and given in Table 1.

TABLE 1

| Polymer or Therapeutic Agent | Hildebrand solubility parameter, $(cal/cm^3)^{1/2}$ |
|---|---|
| Poly(L-lactide-co-ε-caprolactone) (70:30) | 10.85 |
| Poly(L-lactide-co-trimethylene carbonate) (70:30) | 10.94 |
| Everolimus | 11.04 |

In order to control the release of a therapeutic agent, it is preferred that there is at least some miscibility. The release of a therapeutic agent is best controlled by permeation (the product of solubility and diffusivity of drug in polymer). If the therapeutic agent loading exceeds miscibility, the phase separation occurs. When the amount of therapeutic agent exceeds the volumetric percolation limit, the release mechanism is additionally affected by a porous mechanism which can be hard to reproduce. If a therapeutic agent is completely immiscible in the polymer, the polymer encapsulates (isolates) the therapeutic agent and no release occurs except for the therapeutic agent that is on the surface. When the therapeutic agent loading approaches and exceeds percolation, release is mostly by a porous or channel mechanism. Thus, the hydrophobicity of the polymer is critical in dissolving a therapeutic agent, such as without limitation, everolimus. For instance, the hydrophobicity of the polymers can be matched with the hydrophobicity of everolimus thus maximizing the solubility of everolimus and in turn, optimizing the release rate of everolimus from the stent.

EXAMPLES

The embodiments of the present invention can be further illustrated by the following set forth examples. The following examples are provided for illustrative purposes only and are not intended nor should they be construed as limiting the scope of this invention in any manner whatsoever.

Example 1

A composition was prepared by adding poly(L-lactide-co-ε-caprolactone) (0.12 gm) in chloroform (4.6848 g) and trichloroethane (1.17 g) in a tightly closed glass bottle. The mixture was stirred at 250 rpm for 2 hours. Everolimus (0.0245 g) was added to the reaction mixture. The reaction mixture further stirred at 500 rpm for 2 minutes. The first composition is applied onto the stent and dried to form a drug-polymer layer.

The composition is applied onto the stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is from about 100 microgram/cm². The drug reservoir layer coating thickness is 6 um.

Example 2

A composition was prepared by adding poly(L-lactide-co-ε-caprolactone) (0.12 gm) in chloroform (4.67 g) and trichloroethane (1.17 g) in a tightly closed glass bottle. The mixture was stirred at 250 rpm for 2 hours. Everolimus (0.0408 g) was added to the reaction mixture. The reaction mixture further stirred at 500 rpm for 2 minutes. The first composition is applied onto the stent and dried to form a drug-polymer layer.

The composition is applied onto the stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:3. The drug dose is from about 100 microgram/cm². The drug reservoir layer coating thickness is 4 um.

Example 3

A composition was prepared by adding poly(L-lactide-co-trimethylene carbonate) (0.06 gm) in trichloroethane (2.928 g) in a tightly closed glass bottle. The mixture was stirred at 250 rpm for 2 hours. Everolimus (0.01224 g) was added to the reaction mixture. The reaction mixture further stirred at 500 rpm for 2 minutes. The first composition is applied onto the stent and dried to form a drug-polymer layer.

The composition is applied onto the stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is from about 100 microgram/cm². The drug reservoir layer coating thickness is 6 um.

Example 4

A composition was prepared by adding poly(L-lactide-co-trimethylene carbonate) (0.06 gm) in trichloroethane (2.928 g) in a tightly closed glass bottle. The mixture was stirred at 250 rpm for 2 hours. Everolimus (0.01224 g) was added to the reaction mixture. The reaction mixture further stirred at 500 rpm for 2 minutes. The first composition is applied onto the stent and dried to form a drug-polymer layer.

The composition is applied onto the stent by any conventional method, for example, by spraying or dipping. A primer layer (e.g., the above formulation without the therapeutically active substance) can be optionally applied on the surface of the bare stent prior to the application of the drug-polymer layer. The drug to polymer wt/wt ratio is 1:5. The drug dose is from about 50 microgram/cm². The drug reservoir layer coating thickness is 6 um.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:
1. An implantable medical device, comprising:
a device body;
an optional primer layer disposed over the device body;
a drug reservoir layer disposed over the device body or the primer layer, if opted,
wherein the drug reservoir layer comprises a polymer and a therapeutic agent and further wherein the hydrophobicity of the polymer is matched to that of the therapeutic agent so that the therapeutic agent is miscible with the polymer;
wherein the polymer is
poly(L-lactide-co-ε-caprolactone) wherein the molar ratio of L-lactide and ε-caprolactone is from 70:30 to 50:50, or poly(L-lactide-co-trimethylene carbonate) wherein the molar ratio of L-lactide and trimethylene carbonate is 70:30;

wherein the therapeutic agent is everolimus.

2. The implantable medical device of claim 1, wherein the poly(L-lactide-co-ϵ-caprolactone) has an average molecular weight from about 50,000 to about 500,000 Daltons.

3. The implantable medical device of claim 1, wherein the drug reservoir layer has a coating thickness from 1 μm to 10 μm.

4. The implantable medical device of claim 1, wherein the therapeutic agent to polymer wt/wt ratio is from 1.0:0.5 to 1.0:10.0.

5. The implantable medical device of claim 1, wherein the therapeutic agent dose is from 5-200 microgram/cm$^2$ to 20-100 microgram/cm$^2$.

6. The implantable medical device of claim 1, wherein the device is a stent.

7. A method of treating a vascular disease, wherein the vascular disease is selected from the group consisting of atherosclerosis, restenosis, vulnerable plaque, peripheral vascular disease, and late stent thrombosis, wherein the method of treating comprises: deploying in the vasculature of a patient in need thereof an implantable medical device of claim 1.

* * * * *